(12) United States Patent
Styfhoorn et al.

(10) Patent No.: US 9,361,779 B2
(45) Date of Patent: Jun. 7, 2016

(54) REMOTE WATER IN FUEL INDICATOR UNIT (71) Applicant: Caterpillar Inc., Peoria, IL (US)

(72) Inventors: Timothy J. Styfhoorn, Dunlap, IL (US); Nathaniel Kamp, Chillicothe, IL (US); Robert W. Schulz, Peoria, IL (US); Eric R. Strube, Morton, IL (US); Mark T. Allott, Mapleton, IL (US)

(73) Assignee: Caterpillar Inc., Peoria, IL (US)

( * ) Notice: Subject to any disclaimer, the term of this patent is extended or adjusted under 35 U.S.C. 154(b) by 0 days.

(21) Appl. No.: 14/465,916

(22) Filed: Aug. 22, 2014

(65) Prior Publication Data
US 2016/0055738 A1    Feb. 25, 2016

(51) Int. Cl.
*B01D 35/143* (2006.01)
*G08B 21/20* (2006.01)
*G01N 33/28* (2006.01)
*B01D 36/00* (2006.01)

(52) U.S. Cl.
CPC .............. *G08B 21/20* (2013.01); *B01D 35/143* (2013.01); *B01D 36/005* (2013.01); *G01N 33/2847* (2013.01)

(58) Field of Classification Search
CPC ....................................................... G08B 21/20
USPC ......... 340/438, 450, 450.2, 618; 701/29, 29.1
See application file for complete search history.

(56) References Cited

U.S. PATENT DOCUMENTS

| | | | |
|---|---|---|---|
| 4,276,161 A * | 6/1981 | Matsui ............... | B01D 17/0214 210/138 |
| 4,562,431 A * | 12/1985 | Jahnke ................. | G01F 23/241 210/85 |
| 4,728,924 A | 3/1988 | Franklin | |
| 6,676,841 B2 | 1/2004 | Akins et al. | |
| 7,368,060 B2 | 5/2008 | Faxides | |
| 8,496,816 B2 | 7/2013 | True-Dahl et al. | |
| 2004/0069694 A1* | 4/2004 | Gamble ............... | B01D 36/005 210/85 |
| 2010/0117842 A1 | 5/2010 | Fachidis | |
| 2012/0162654 A1 | 6/2012 | Webb et al. | |
| 2014/0202580 A1* | 7/2014 | Hutchinson ............ | B67D 7/342 141/1 |

FOREIGN PATENT DOCUMENTS

EP          0497373         1/1992

OTHER PUBLICATIONS

Fuel Water Sensor, from Dieselcraft™, 1 page, downloaded from http://www.dieselcraft.com/fuel-water-sensor.php, retrieved using Internet Archive: Wayback Machine (archive.org/web) entry dated Jul. 2, 2013.

* cited by examiner

*Primary Examiner* — Brent Swarthout

(57) ABSTRACT

A positionable water in fuel indicator unit including an indicator housing having a back panel, and a housing cover connected to the back panel. The water in fuel indicator unit can also include a signal receiving device configured to receive a water in fuel signal from a water in fuel sensor located in the fuel filter, a first indicator visible through the housing cover and configured to indicate when a water level in the fuel filter is less than a predetermined threshold, a second indicator visible through the housing cover and configured to indicate when the water level in the fuel filter is equal to or greater than the predetermined threshold, and a controller enclosed by the housing cover. The controller can be configured to activate the first indicator based on the water in fuel signal, and activate the second indicator based on the water in fuel signal.

17 Claims, 9 Drawing Sheets

REMOTE WATER IN FUEL INDICATOR UNIT

TECHNICAL FIELD

The present disclosure relates generally to a water in fuel indicator. More specifically, the present disclosure relates to a remote water in fuel indicator unit.

BACKGROUND

Fuels used to power engines may have a variety of contaminants that need to be removed prior to the fuel being introduced to the combustion chamber of an engine. Typically, filtration devices are utilized to remove these contaminants. Fuel, and in particular diesel fuel, residing in a fuel tank may have water present that needs to be removed prior to being introduced into the engine. The water may be naturally present in the fuel, or the water may be formed from condensation. Certain fuel filters may be utilized to separate water from the fuel for this purpose. These fuel filters may have a limited capacity to store the separated water. If the water is not timely drained from the fuel filter, the efficacy of the fuel filter in removing water from the fuel may be compromised. Therefore, the water will need to be drained from the fuel filter to ensure continued proper function of the fuel filter.

One attempt to notify an operator that the water in the fuel filter may need to be drained is described in U.S. Pat. No. 6,676,841, which issued to Akins et al. on Jan. 13, 2004 ("the '841 patent"). The '841 patent describes providing a warning light in a dashboard of a machine which indicates when the water needs to be drained from the fuel filter. However, in a machine that does not have the warning light already implemented in the dashboard, it can be expensive to add such a system. Furthermore, the location of the warning light may not be in a convenient and easily visible location for mechanics, or other service technicians that may perform maintenance on the machine.

The system and method of the present disclosure solves one or more problems set forth above and/or other problems in the art.

SUMMARY

In one aspect, the present disclosure is directed to a positionable water in fuel indicator unit including an indicator housing having a back panel, and a housing cover connected to the back panel. The water in fuel indicator unit can also include a signal receiving device configured to receive a water in fuel signal from a water in fuel sensor located in the fuel filter, a first indicator visible through the housing cover and configured to indicate when a water level in the fuel filter is less than a predetermined threshold, a second indicator visible through the housing cover and configured to indicate when the water level in the fuel filter is equal to or greater than the predetermined threshold, and a controller enclosed by the housing cover. The controller can be configured to activate the first indicator based on the water in fuel signal, and activate the second indicator based on the water in fuel signal.

In another aspect, the present disclosure is directed a positionable water in fuel indicator unit including a reset unit configured to generate a reset signal when activated, a first indicator, a second indicator, and a controller located remotely from a fuel filter. The controller can be configured to receive a water in fuel signal from a water in fuel sensor located in the fuel filter using a signal receiving device, activate the first indicator when the water in fuel signal indicates that a water level in the fuel filter is less than a predetermined threshold, activate the second indicator when the water in fuel signal indicates that the water level in the fuel filter is equal to or greater than the predetermined threshold, receive the reset signal, and deactivate the second indicator when the reset signal is received.

In another aspect, the present disclosure is directed to a method for providing an indication as to when to drain water from a fuel filter, the method including receiving a water in fuel signal from a water in fuel sensor located in the fuel filter, activating a first indicator in a positionable water in fuel indicator unit located remotely from the fuel filter when the water in fuel signal indicates that a water level in the fuel filter is less than a predetermined threshold, activating the second indicator when the water in fuel signal indicates that the water level in the fuel filter is equal to or greater than the predetermined threshold, receiving a reset signal from a reset unit in the water in fuel indicator, and deactivating the second indicator when the reset signal is received.

DETAILED DESCRIPTION

Figure 1:
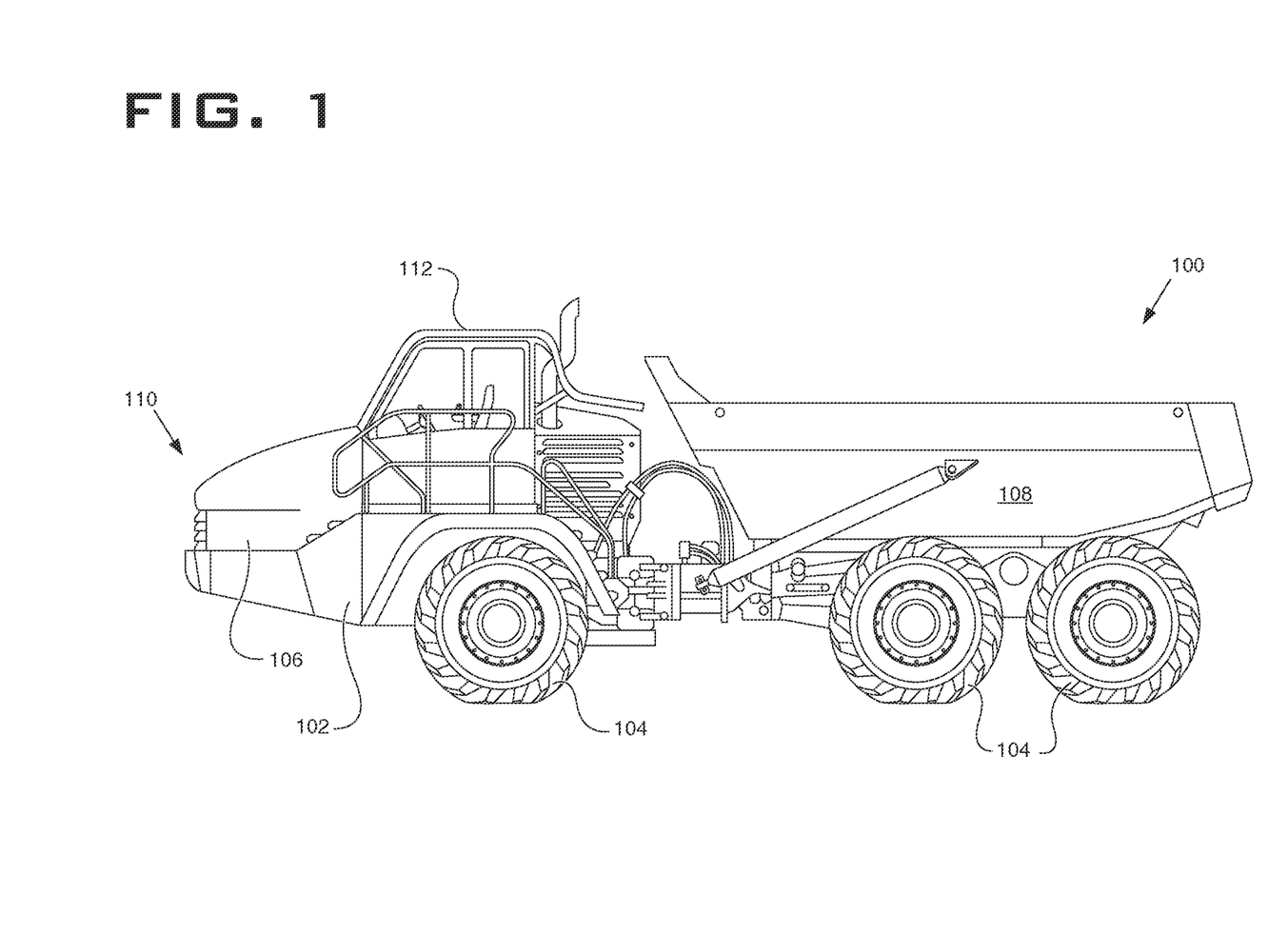
FIG. 1 depicts a machine according to an embodiment.

Wherever possible, the same reference numbers will be used throughout the drawings to refer to the same or the like parts. FIG. 1 illustrates a machine 100. In one embodiment, the machine 100 may embody an articulated truck. Alternatively, the machine 100 may include a track-type tractor, a hydraulic excavator, a wheel loader, a haul truck, a large mining truck, an off-highway truck, and the like. It should be understood that the machine 100 may embody any wheeled or tracked machine associated with mining, agriculture, forestry, construction, and other industrial applications. Furthermore, although the machine 100 is shown and used in the description below, the machine 100 is merely exemplary and an equipment that utilizes a stationary engine, a generator, or any combination thereof, may also be utilized.

As illustrated in FIG. 1, the machine 100 may be a wheeled machine and includes a frame 102, wheels 104, an engine compartment 106, and a payload carrier 108. The machine 100 may further include an engine positioned in the engine compartment 106 and supported on the frame 102. The engine may be an internal combustion engine such as, for example, a reciprocating piston engine or a gas turbine engine. According to one embodiment of the present disclosure, the engine is a spark ignition engine or a compression ignition engine such as, a diesel engine, a homogeneous charge compression ignition engine, or a reactivity controlled compression ignition engine, or other compression ignition engine known in the art. The engine may be fueled by diesel, fuel that contains water, fuel that needs water removed, or any combination thereof. In the illustrated embodiment, a cab 112 is mounted on a front end 110 of the frame 102 of the machine 100.

Figure 2:
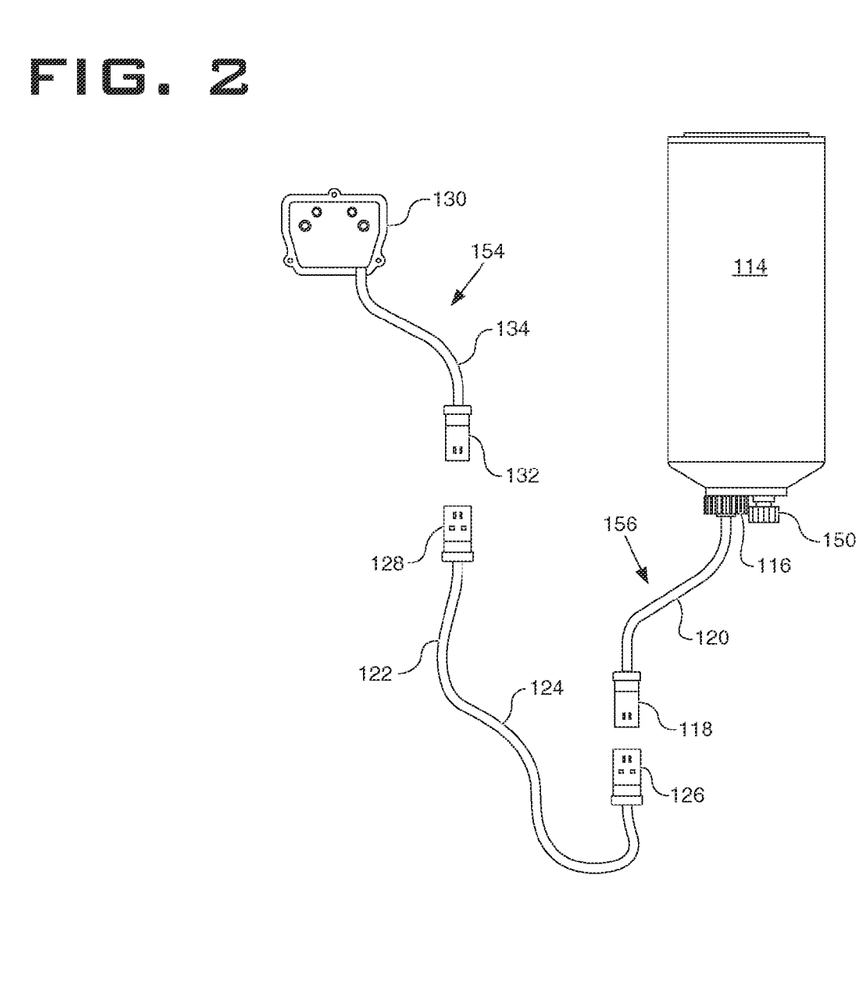
FIG. 2 depicts a water in fuel indicator unit and a fuel filter according to an embodiment.

Referring now to FIG. 2 in addition to FIG. 1, a fuel filter 114 may be mounted in the engine compartment 106 to remove contaminants from the fuel that will be introduced into the engine. The fuel filter 114 can comprise a water in fuel filter that at least in part functions to separate water from the fuel. The fuel can be, for example, diesel fuel, however, other types of fuel which contain water or which need water to be removed, may be utilized instead. The water separated from the fuel can be collected by the fuel filter 114 in a lower section 136, such as a bowl. When there is too much water collected in the lower section 136 of the fuel filter 114, the collected water can be drained by utilizing a drain unit 150 that communicates between the interior of the lower section 136 and the environments outside of the fuel filter 114, which will be described in more detail later.

To determine when the collected water in the fuel filter 114 should be drained from fuel filter 114, a water in fuel sensor 116 may be utilized. The water in fuel sensor 116 can generate a signal indicating a water level in the fuel filter 114. For example, the water in fuel signal can indicate a water level in the fuel filter 114 relative to a predetermined threshold. In addition, the water in fuel signal can indicate when the water level in the fuel filter 114 is less than a predetermined threshold, or greater than or equal to the predetermined threshold. As such, the predetermined threshold can be selected to increase the likelihood that the collected water in the fuel filter 114 is timely drained and thereby avoids the level of water in the filter exceeding a point where the fuel filter 114 no longer functions properly.

The water in fuel sensor 116 can transmit the water in fuel signal using a signal communication device 156. In an exemplary embodiment, the signal communication device 156 comprises a wire 120 and a connector 118. However, the signal communication device 156 can also comprise a wireless transmission unit such as a transceiver. The wireless transmission unit can be configured to transmit data using one or more protocols such as WiFi, BLUETOOTH™, near field authentication, or other types of protocols which can facilitate wireless transmission of data. In an embodiment, the signal communication device 156 can comprise a port extending from the fuel filter 114. In such a case, the wire 120 may be optional or have a short length. For example, the wire 120 may be located entirely within the fuel filter 114 while the connector 118 is located completely or partially outside the fuel filter 114.

A water in fuel indicator unit 130 can receive the water in fuel signal from the water in fuel sensor 116 using a signal receiving device 154 connectable to the signal communication device 156. Similarly, the signal receiving device 154 can comprise a wire 134 and a connector 132. The connector 132 can have mating surfaces that engage connector 118 of the signal communication device 156 and allow signal transmission to pass from the signal communication device 156 to the signal receiving device 154. The signal receiving device 154 can also comprise a wireless receiving unit such as a transceiver. The transceiver for the signal receiving device 154 can be similar to the transceiver for the signal communication device 156.

Optionally, a wiring extension 124 may be provided to connect the water in fuel sensor 116 and the water in fuel indicator unit 130 in order to span longer distances than the respective wires 120 and 134 of the signal communication device 156 and the signal receiving device 154. The wiring extension 124 can comprise a wire 122 and connectors 128 and 126. The connector 126 can be configured to engage the connector 118 while the connector 128 can be configured to engage to the connector 132. In an embodiment, the wiring extension 124 can extend a distance between the water in fuel sensor 116 and the water in fuel indicator unit 130 by providing an extended connection between the water in fuel sensor 116 and the water in fuel indicator unit 130.

Figure 3:
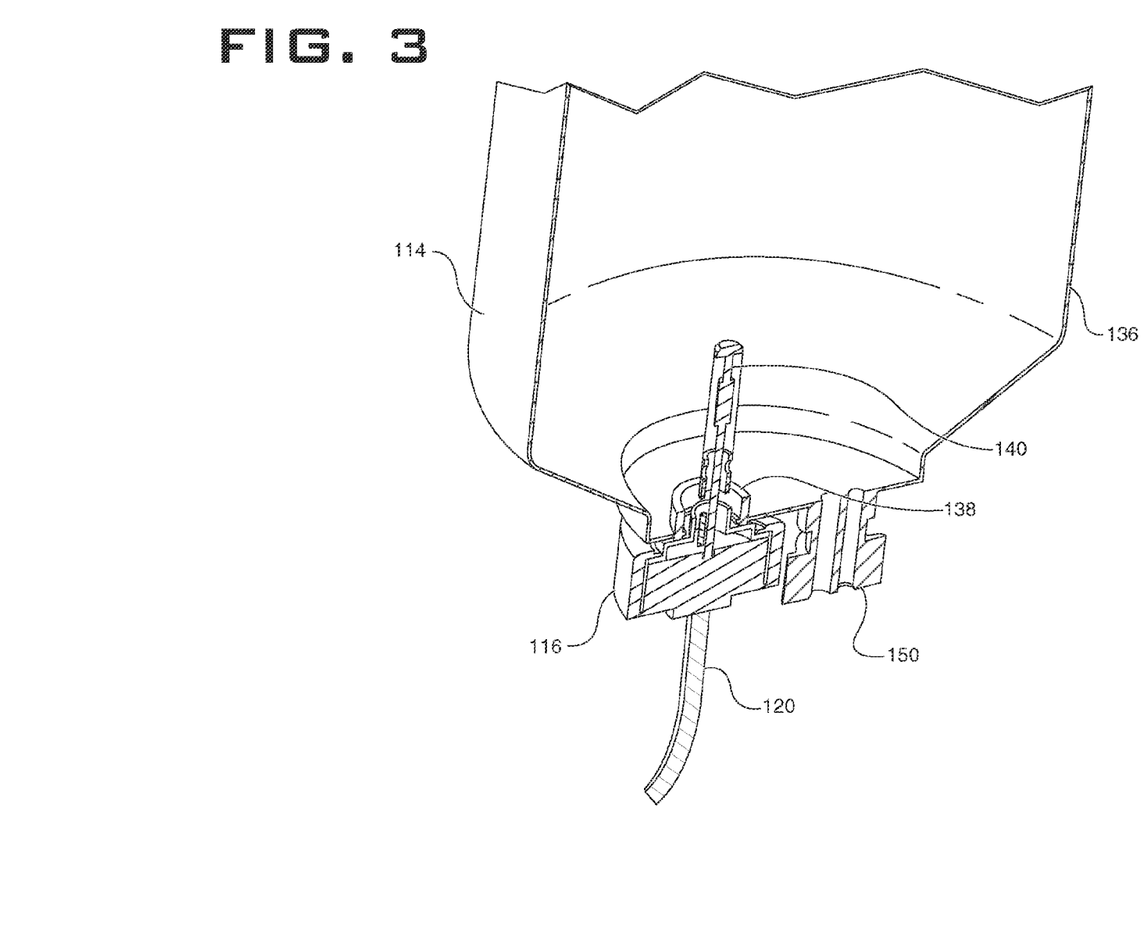
FIG. 3 depicts a portion of a fuel filter according to an embodiment.

Referring to FIG. 3, the fuel filter 114 comprises a lower section 136, such as a bowl, which is used to collect water. The lower section 136 comprises an aperture 138 through which the water in fuel sensor 116 extends into the lower section 136. In an embodiment, the water in fuel sensor 116 can detect a water level in the fuel filter 114 based on the conductivity of the type of fluid the sensing portion of the sensor is encountering. For example, when the water level is above or equal to a predetermined threshold, a circuit may be completed because the ability of water to conduct an electrical current is greater than that of the fuel that is being filtered. However, when the water level is below the predetermined threshold, the circuit may be open or the current passed through the fuel is less than when water is present. In addition, the water in fuel sensor 116 can detect the water level in alternate methods through electromagnetic means, mechanical means, or any combination thereof. As previously noted, the collected water in the fuel filter 114 can be drained from the lower section 136 using the drain unit 150.

Figure 4:
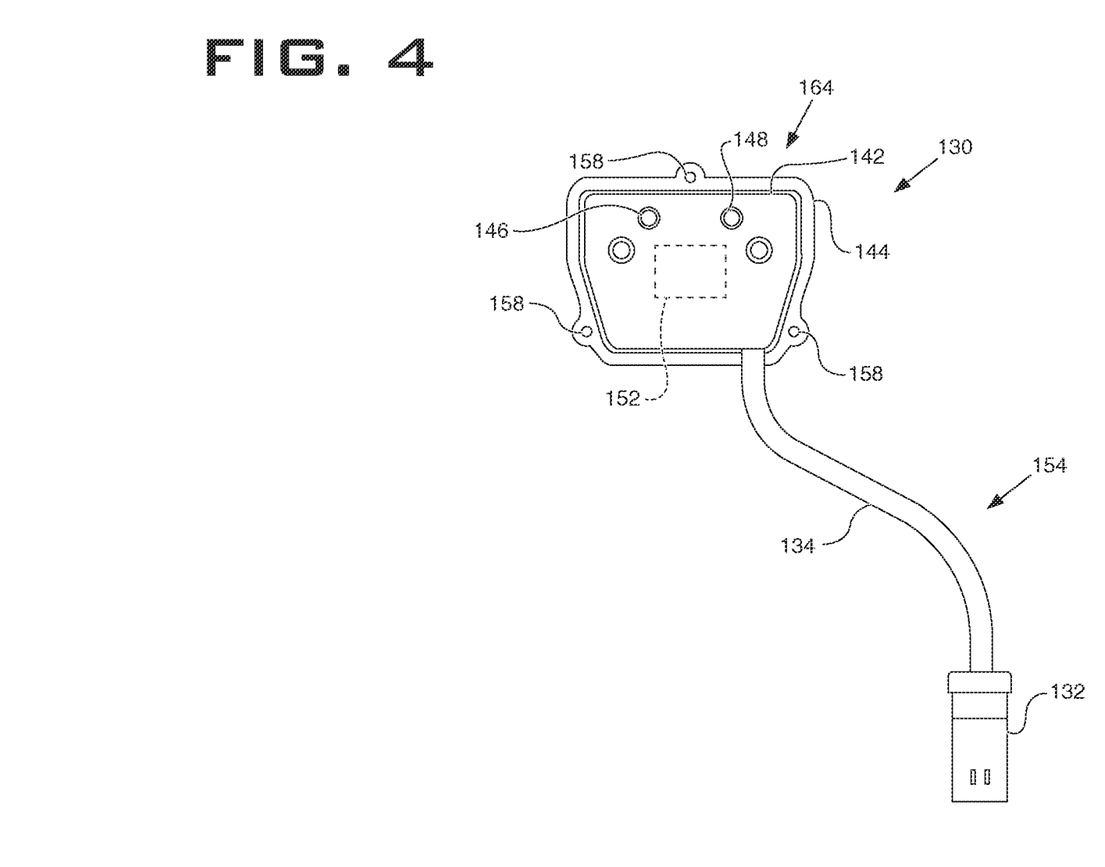
FIG. 4 depicts a first side of a water in fuel indicator unit according to an embodiment.
Figure 5:
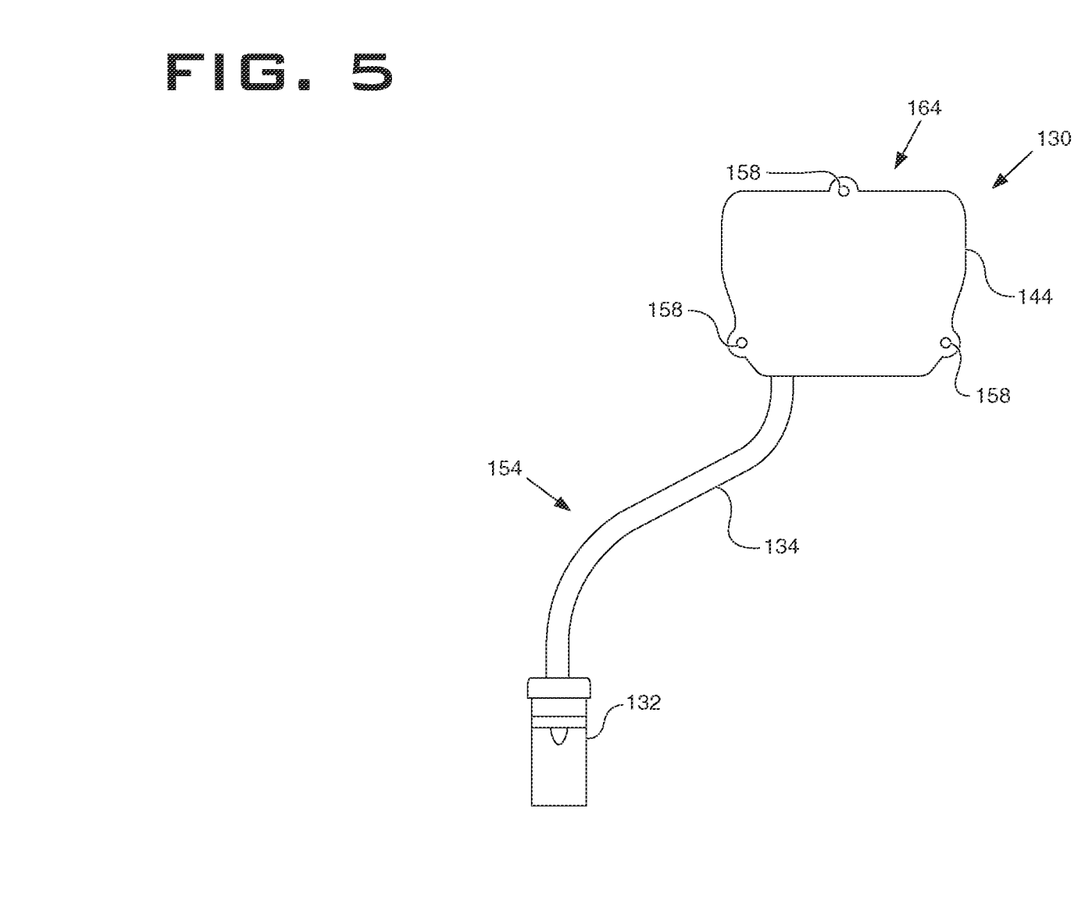
FIG. 5 depicts a second side of the water in fuel indicator unit of FIG. 4.

Referring to FIGS. 4 and 5, a first side and a second side of the water in fuel indicator unit 130 is shown. FIG. 4 depicts the first side of the water in fuel indicator unit 130, while FIG. 5 depicts the second side of the water in fuel indicator unit 130. The water in fuel indicator unit 130 can comprise a positionable water in fuel indicator unit.

The water in fuel indicator unit 130 comprises a housing 164 such as an indicator housing. The housing 164 can comprise a housing cover 142 connected to a back panel 144. The back panel 144 can comprise securing mechanisms 158 which can be used to connect the back panel 144, the housing cover 142, and the water in fuel indicator unit 130 to a surface. The surface can be, for example, a surface on the machine 100. The securing mechanisms 158 can comprise one or more apertures which can be used in conjunction with fasteners to secure the back panel 144, the housing cover 142, and the water in fuel indicator unit 130 to the surface. The fasteners can comprise screws, nails, bolts, or other devices which can be used to secure the back panel 144, the housing cover 142, and the water in fuel indicator unit 130 to the surface. In an alternative embodiment, the securing mechanisms 158 can also comprise a hook and loop fastener or portions of a hook and loop fastener.

The surface can be a location on the machine 100 which is visible to a user. The surface can also be located in an interior or an exterior of the machine 100, for example in the interior of the cab 112 or within the engine compartment 106 proximal to the location of the fuel filter 114. However, in an embodiment, the securing mechanisms 158 are optional and need not be used, such as if the water in fuel indicator unit 130 comprises a portable unit.

The water in fuel indicator unit 130 can also comprise a first indicator 146 and a second indicator 148. The first indicator 146 can be visible through the housing cover 142 and configured to indicate when a water level in the fuel filter 114 is less than a predetermined threshold. The second indicator 148 can be visible through the housing cover 142 and configured to indicate when the water level in the fuel filter 114 is equal to or greater than the predetermined threshold.

In an embodiment, the first indicator 146 can provide a first indication when the first indicator 146 is activated, and the second indicator 148 can provide a second indication different than the first indication when the second indicator 148 is activated. For example, the first indication can include displaying a first color, while the second indication can include displaying a second color different than the first color. However, the first indication can also comprise displaying a flashing light of a first pattern, while the second indication can also comprise displaying a flashing light of a second pattern different than the first pattern.

The water in fuel indicator unit 130 can also comprise a reset unit 152. The reset unit 152 can be configured to generate a reset signal when activated. The reset signal can indicate when the second indicator 148 should be deactivated. The reset unit 152 can be configured to generate the reset signal based at least on a presence of an object proximate the reset unit 152 for a period of time greater than a predetermined period of time threshold. For example, when a user places a finger proximate the reset unit 152 for a period of time greater than a predetermined period of time threshold, the reset unit 152 can generate the reset signal. In an embodiment, the reset unit 152 can require the depression of the reset unit 152 before the reset signal is generated. The reset unit 152 can be located at least partially within the housing 164. Although the reset unit 152 is located generally between the first indicator 146 and the second indicator 148 in FIG. 4, the reset unit 152 can be located elsewhere within, or on the surface of the housing 164.

In an embodiment, the reset unit 152 can comprise a button which can be depressed. The reset unit 152 can also comprise a sensor which detects a presence of an object.

Figure 6:
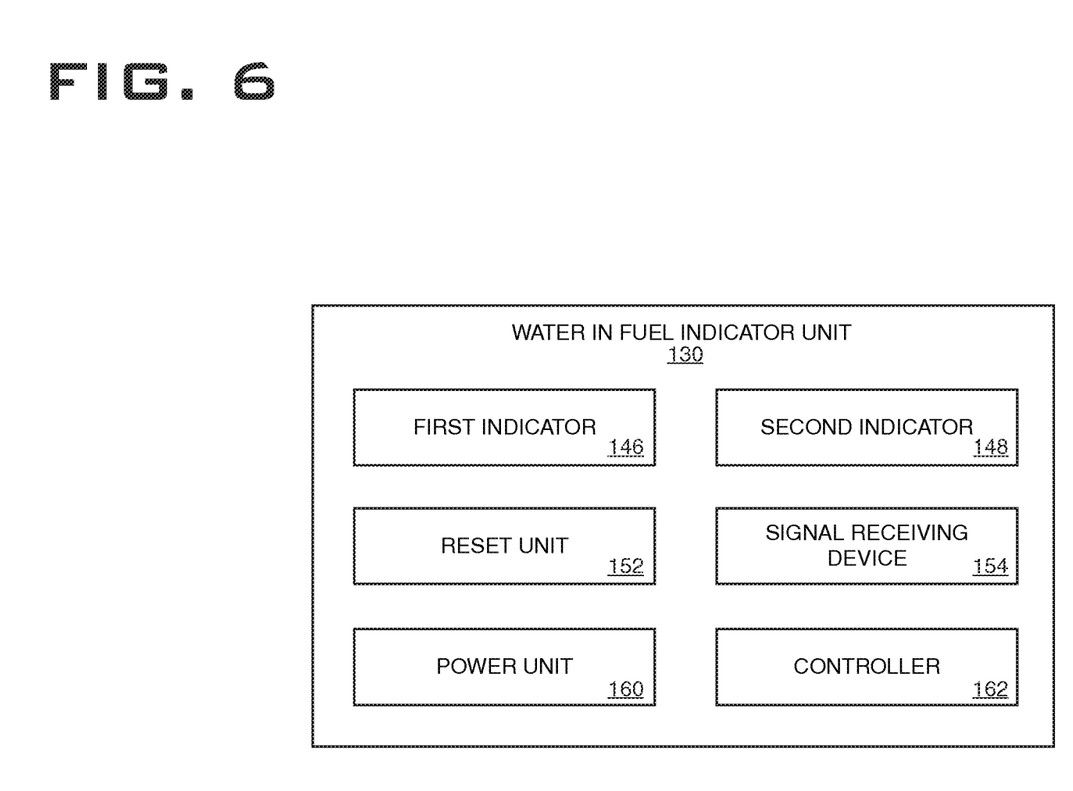
FIG. 6 is a box diagram of a water in fuel indicator unit according to an embodiment.

Referring now to FIG. 6, the water in fuel indicator unit 130 can also comprise a power unit 160 and a controller 162. In an embodiment, the power unit 160 can comprise a limited power source such as a battery. The power unit 160 can be configured to power the first indicator 146, the second indicator 148, the reset unit 152, the signal receiving device 154, the controller 162, other components of the water in fuel indicator unit 130, or any combination thereof. In an embodiment, the power unit 160 is configured to be located within the housing 164. Thus, the water in fuel indicator unit 130 can also be a modular or portable unit which can be powered through the power unit 160 instead of through the machine 100.

The controller 162 can be configured to control operations of the first indicator 146, the second indicator 148, the reset unit 152, the signal receiving device 154, or any combination thereof. In an embodiment, the controller 162 can comprise a processor. The processor can also be connected to a memory. The memory can comprise a volatile or a non-volatile memory. Furthermore, the memory can be configured to store code which can be executed by the processor to perform one or more functions, or data which can be utilized by the processor to perform one or more functions.

In an embodiment the controller 162 can activate or deactivate the first indicator 146 or the second indicator 148 based on a water level in the fuel filter 114. For example, the controller 162 can activate or deactivate the first indicator 146 or the second indicator 148 based on the water in fuel signal. The controller 162 can also deactivate the second indicator 148 based on the reset signal from the reset unit 152. In an embodiment, the controller 162 can also deactivate the second indicator 148 based on the signals from the water in fuel sensor 116. For example, when the water in fuel sensor 116 indicates that the water level in the fuel filter 114 is less than the predetermined threshold.

Figure 8:
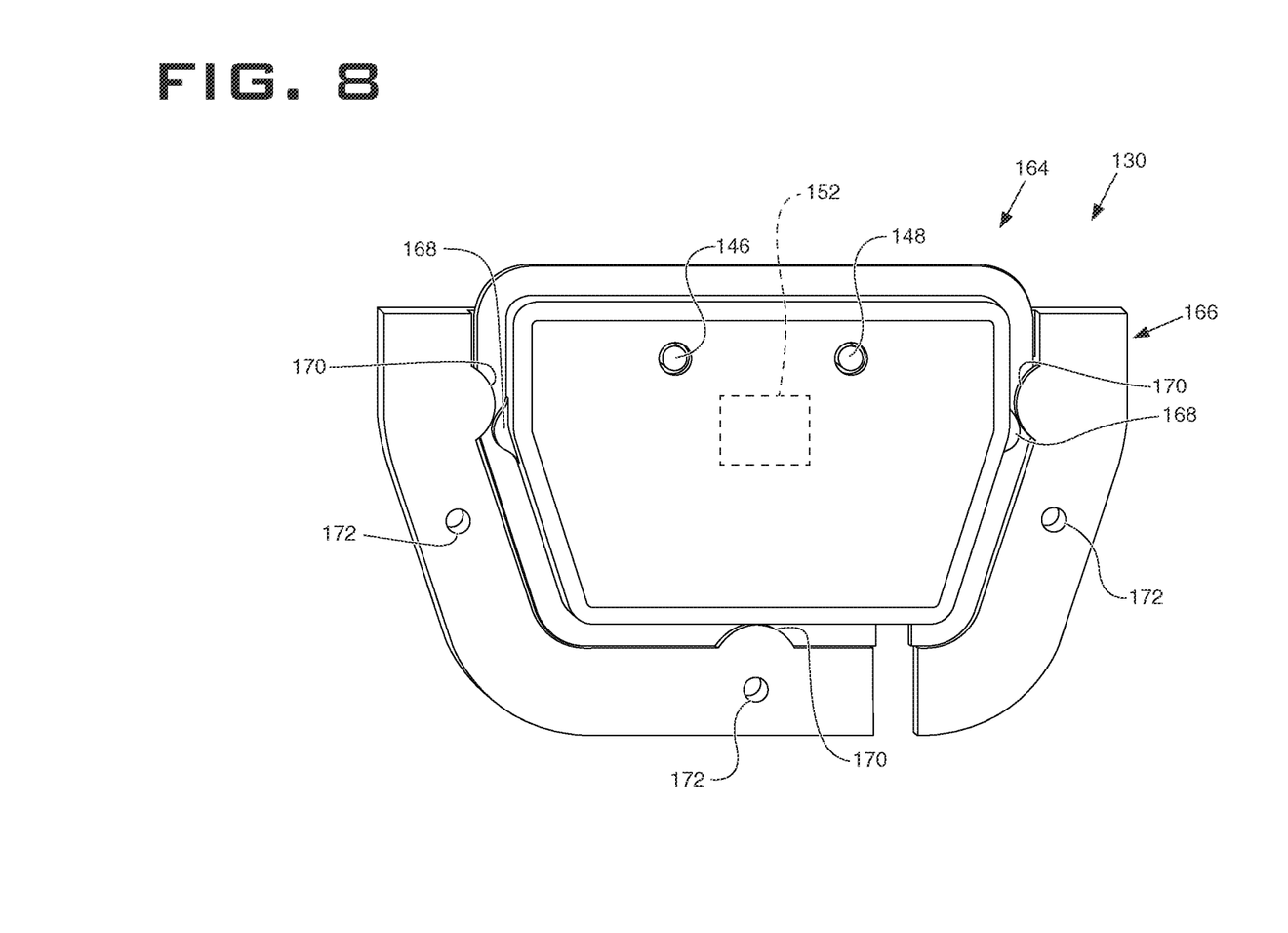
FIG. 8 depicts a first side of a water in fuel indicator unit and a bracket according to an embodiment.
Figure 9:
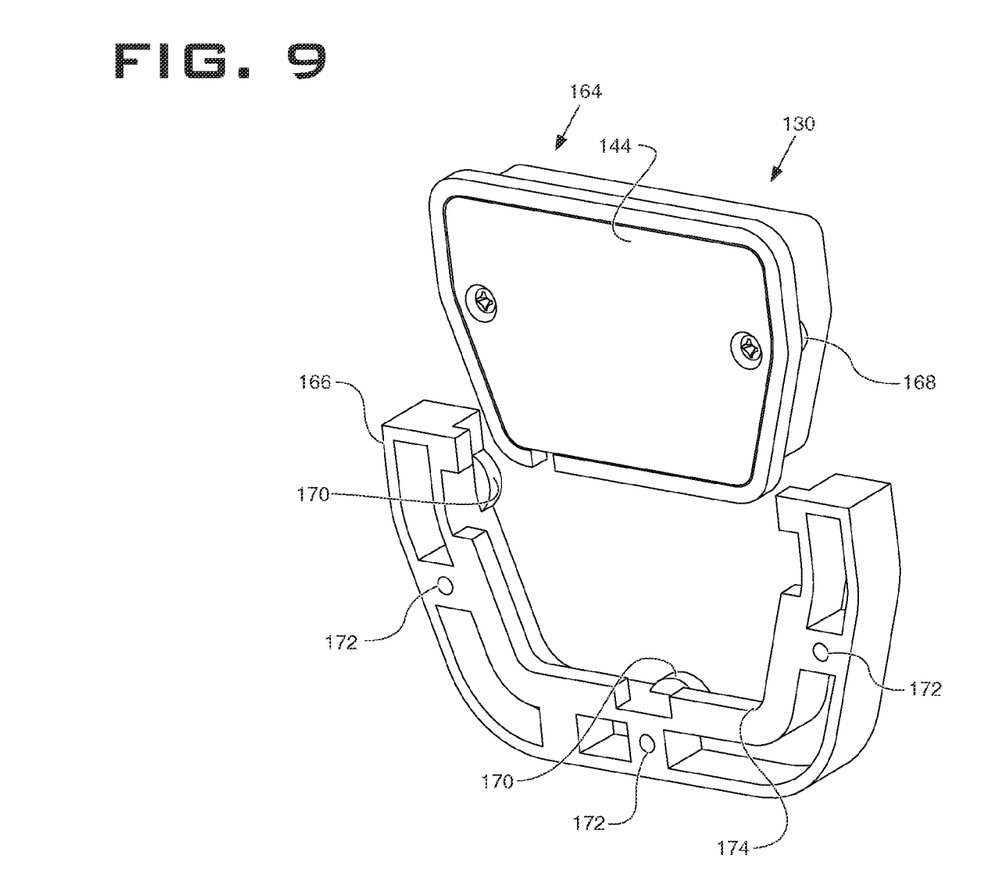
FIG. 9 depicts a perspective view of a water in fuel indicator unit and a bracket of FIG. 8 from a second side according to an embodiment.

In an embodiment, as shown in FIGS. 8 and 9, the water in fuel indicator unit 130 can be mounted to the machine 100 using a bracket 166 instead of the securing mechanisms 158. The bracket 166 can comprise securing mechanisms 172 to mount the bracket 166 to the machine 100. The water in fuel indicator unit 130 can then be removably inserted into the bracket 166. Although the signal receiving unit 154 is not shown, the water in fuel indicator unit 130 can still utilize the signal receiving unit 154.

The bracket 166 can then retain the water in fuel indicator unit 130 using a retention ridge 174. To further aid in retaining the water in fuel indicator 130 to the bracket 166, the water in fuel indicator unit 130 can include a first set of retention units 168, while the bracket 166 can include a second set of retention units 170. The retention ridge 174, the first set of retention units 168 and the second set of retention units 170 can cooperate with each other to retain the water in fuel indicator 130 to the bracket 166.

The water in fuel indicator 130 can slide onto the bracket 166, or a snap fit may be formed between the water in fuel indicator 130 and the bracket 166. Furthermore, in an embodiment, the bracket 166 may be considered to be part of the water in fuel indicator 130.

INDUSTRIAL APPLICABILITY

In general, the foregoing disclosure finds utility in various applications relating to water removal in the fuel filter 114. More specifically, the disclosed systems and methods may be used to indicate when the fuel filter 114 should be drained of water. In addition, the disclosed systems and methods may also allow the fuel filter 114 to be located in portions of the machine 100 which are not easily visible. The fuel filter 114 can also comprise materials which are not translucent and which may be more durable. Furthermore, even when the fuel filter 114 comprises a clear bowl for visual indication of a water level inside the bowl, the clear bowl can become obscured by surface dirt or material. This can obscure the water level such that it is not visible or easily ascertainable through a visual inspection. The water in fuel sensor 116 can be installed in the aperture of the clear bowl and used with the water in fuel indicator 130 to convert the fuel filter 114 from a visual to an electronic water detection.

In an embodiment, the machine 100 can comprise a track-type tractor, a hydraulic excavator, a wheel loader, a haul truck, a large mining truck, an off-highway truck, and the like. However, in an embodiment, the disclosed systems and methods may also be used with stationary engines, generators, or any combination thereof, which utilize diesel fuel and the fuel filter 114.

Furthermore, by utilizing the water in fuel indicator unit 130, an operator can drain the water in the fuel filter 114 in a more timely manner. This can reduce the likelihood of issues resulting from water accumulation in the fuel filter 114 and ensure that the fuel filter 114 continues to function properly.

In addition, when the water in fuel indicator unit 130 is a portable unit, the water in fuel indicator unit 130 can be utilized to service multiple fuel filters and multiple machines. For example, the signal receiving device 154 can be configured to connect to a first signal communication device in a first fuel filter, and a second signal communication device in a second fuel filter. The first fuel filter and the second fuel filter can be separate fuel filters. This can reduce a cost of maintaining the multiple fuel filters and the multiple machines.

Figure 7:
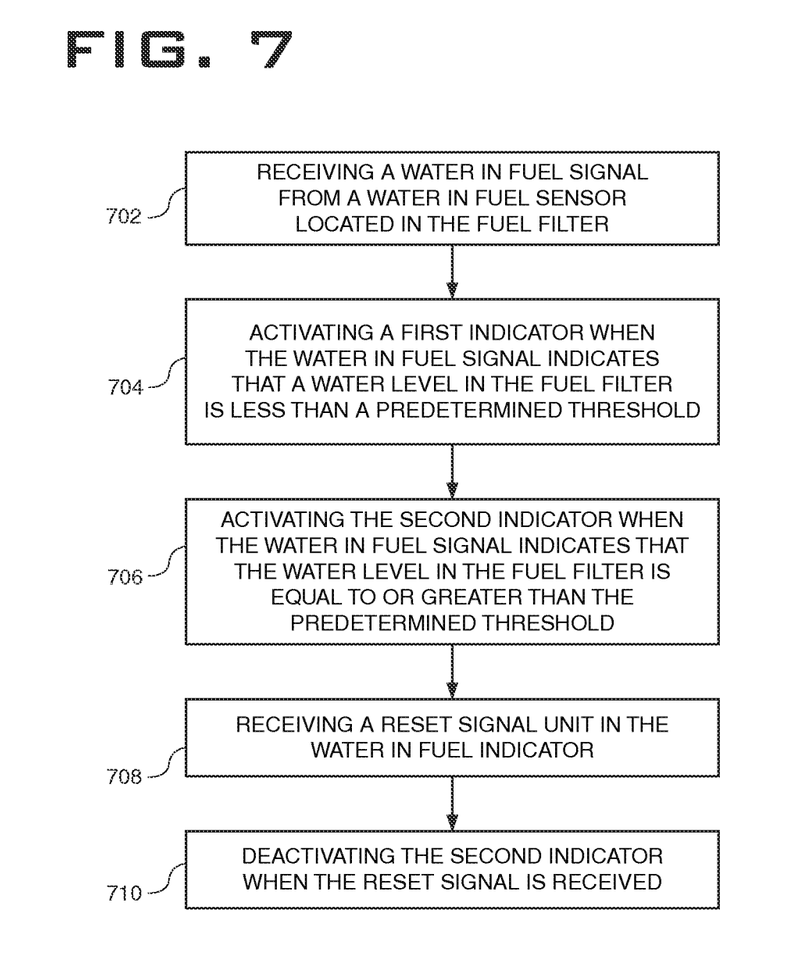
FIG. 7 depicts a process for operating a water in fuel indicator unit.

In an embodiment, a process for operating the water in fuel indicator unit 130 is shown in FIG. 7. The controller 162 can receive in 702 the water in fuel signal from the water in fuel sensor 116 located in the fuel filter 114. When the water in fuel signal is received, the controller 162 can activate in 704 the first indicator 146 when the water in fuel signal indicates that the water level in the fuel filter 114 is less than a predetermined threshold.

The controller 162 can activate in 706 the second indicator 148 when the water in fuel signal indicates that the water level in the fuel filter 114 is equal to or greater than the predetermined threshold. As previously noted, the first indicator 146 can provide the first indication, while the second indicator 148 can provide the second indication different than the first indication. When the second indicator 148 is activated, this can provide an indication that the fuel filter 114 should be drained of water.

The controller 162 can receive in 708 the reset signal from the reset unit 152. The controller 162 can deactivate in 710 the second indicator 148 when the reset signal is received.

It will be apparent to those skilled in the art that various modifications and variations can be made to the disclosed system and method. Other embodiments will be apparent to those skilled in the art from consideration of the specification and practice of the disclosed system and method. It is intended that the specification and examples be considered as exemplary only, with a true scope being indicated by the following claims.

What is claimed is:

1. A positionable water in fuel indicator unit comprising:
   an indicator housing comprising:
      a back panel, and
      a housing cover connected to the back panel;
   a signal receiving device configured to receive a water in fuel signal from a water in fuel sensor located in a fuel filter
   a first indicator visible through the housing cover and configured to indicate when a water level in the fuel filter is less than a predetermined threshold;
   a second indicator visible through the housing cover and configured to indicate when the water level in the fuel filter is equal to or greater than the predetermined threshold; and
   a controller enclosed by the housing cover and configured to:
      activate the first indicator based on the water in fuel signal, and
      activate the second indicator based on the water in fuel signal,
   wherein a reset unit is configured to generate a reset signal based at least on a presence of an object proximate the reset unit for a period of time greater than a predetermined period of time threshold, and the controller is configured to deactivate the second indicator when the controller receives the reset signal.

2. The positionable water in fuel indicator unit of claim 1 wherein the back panel is configured to be connected to a surface.

3. The positionable water in fuel indicator unit of claim 1 wherein the signal receiving device comprises a wire and a connector.

4. The positionable water in fuel indicator unit of claim 1 further comprising a power unit configured to power the first indicator, the second indicator, and the controller, wherein the power unit comprises a limited power source.

5. The positionable water in fuel indicator unit of claim 1 further comprising a bracket configured to be connected to a surface, and to retain the indicator housing, wherein the indicator housing is removably inserted into the bracket.

6. The positionable water in fuel indicator unit of claim 1 wherein indication by the second indicator signals that the fuel filter should be drained of water.

7. The positionable water in fuel indicator unit of claim 1 wherein the first indicator provides a first indication when the first indicator is activated, and the second indicator provides a second indication different than the first indication when the second indicator is activated.

8. The positionable water in fuel indicator unit of claim 7 wherein the first indication comprises displaying a first color and the second indication comprises displaying a second color different than the first color.

9. A positionable water in fuel indicator unit comprising:
   a reset unit configured to generate a reset signal when activated;
   a first indicator;
   a second indicator; and
   a controller located remotely from a fuel filter and configured to:
      receive a water in fuel signal from a water in fuel sensor located in the fuel filter using a signal receiving device,
      activate the first indicator when the water in fuel signal indicates that a water level in the fuel filter is less than a predetermined threshold,
      activate the second indicator when the water in fuel signal indicates that the water level in the fuel filter is equal to or greater than the predetermined threshold,
      receive the reset signal, and
      deactivate the second indicator when the reset signal is received,
   wherein the reset unit is configured to generate the reset signal based at least on a presence of an object proximate the reset unit for a period of time greater than a predetermined period of time threshold.

10. The positionable water in fuel indicator unit of claim 9 further comprising a power unit configured to power the first indicator, the second indicator, and the controller.

11. The positionable water in fuel indicator unit of claim 10 wherein the power unit comprises a limited power source.

12. The positionable water in fuel indicator unit of claim 9 further comprising an indicator housing comprising:
   a back panel, and
   a housing cover connected to the back panel and configured to be mounted to a machine, wherein the controller is located at least partially in the housing cover, the first indicator is visible through the indicator housing, and the second indicator is visible through the indicator housing.

13. The positionable water in fuel indicator unit of claim 9 further comprising the signal receiving device configured to be connected to the water in fuel sensor, and to receive the water in fuel signal from the water in fuel sensor, wherein indication by the second indicator signals that the fuel filter should be drained of water.

14. The positionable water in fuel indicator unit of claim 9 wherein the first indicator provides a first indication when the first indicator is activated, and the second indicator provides a second indication different than the first indication when the second indicator is activated.

15. The positionable water in fuel indicator unit of claim 14 wherein the first indication comprises displaying a first color and the second indication comprises displaying a second color different than the first color.

16. A method for providing an indication as to when to drain water from a fuel filter, the method comprising:
receiving a water in fuel signal from a water in fuel sensor located in the fuel filter,
activating a first indicator in a positionable water in fuel indicator unit located remotely from the fuel filter when the water in fuel signal indicates that a water level in the fuel filter is less than a predetermined threshold,
activating the second indicator when the water in fuel signal indicates that the water level in the fuel filter is equal to or greater than the predetermined threshold,
generating a reset signal based at least on a presence of an object proximate the reset unit for a period of time greater than a predetermined period of time threshold,
receiving the reset signal from a reset unit in the water in fuel indicator, and
deactivating the second indicator when the reset signal is received.

17. The method of claim 16 further comprising: providing a first indication when the first indicator is activated, and
providing a second indication different than the first indication when the second indicator is activated.

* * * * *